United States Patent [19]

Goldstein et al.

[11] 4,215,111

[45] Jul. 29, 1980

[54] PEPTIDES HAVING UBIQUITIN-LIKE ACTIVITY

[75] Inventors: Gideon Goldstein, Short Hills; George Heavner, Flemington, both of N.J.

[73] Assignee: Ortho Pharmaceutical Corporation, Raritan, N.J.

[21] Appl. No.: 20,157

[22] Filed: Mar. 14, 1979

[51] Int. Cl.$^2$ .................... A61K 37/00; C07C 103/52
[52] U.S. Cl. .............................. 424/177; 260/112.5 R
[58] Field of Search .................. 424/177; 260/112.5 R

[56] References Cited

U.S. PATENT DOCUMENTS 4,113,858  9/1978  Hashim ................................ 424/177

Primary Examiner—Delbert R. Phillips
Attorney, Agent, or Firm—Geoffrey G. Dellenbaugh

[57] ABSTRACT

Peptides of the following formula:

A-B wherein A is a member selected from the group consisting of deamino-GLN, GLN, and (SAR)$_n$-GLN; n is an integer from 1 to 4; and B is a member selected from the group consisting of LYS-OH, LYS-NH$_2$, decarboxy-LYS,

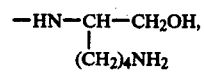

LYS-SAR-OH and LYS-SAR-NH$_2$, have significantly increased ubiquitin-like activity. Also provided are therapeutic compositions and methods for use thereof.

19 Claims, No Drawings

PEPTIDES HAVING UBIQUITIN-LIKE ACTIVITY

BACKGROUND OF THE INVENTION

1. Field of the Invention

This invention relates generally to new peptides, therapeutic compositions containing the same, and methods for use thereof.

2. Description of the Prior Art

U.S. Pat. No. 4,002,602 entitled "Ubiquitous Immunopoietic Polypeptide and Methods", of which one of the present Applicants is the named inventor, discloses the long-chain polypeptide ubiquitin (called therein Ubiquitous Immunopoietic Polypeptide). U.S. patent application Ser. No. 851,778, filed Nov. 15, 1977, of which one of the present Applicants is one of the named inventors, discloses the pentapeptide of sequence H-X-Y-Z-GLN-LYS-OH, wherein X is TYR or ALA, Y is ASN or ALA, and Z is ILE or ALA. This patent application discloses that this pentapeptide has biological activity similar to that of the long-chain polypeptide known as ubiquitin. The above patent and patent application are incorporated herein by reference. The pentapeptide of formula H-TYR-ASN-ILE-GLN-LYS-OH (sometimes referred to herein as the "ubiquitin pentapeptide"), which was the most active compound disclosed in the reference application, showed activity in the mouse assay of Example II thereof at concentrations ranging from 10 ng/ml to 1 μg/ml. The pentapeptides of formula H-ALA-ASN-ILE-GLN-LYS-OH, H-TYR-ALA-ILE-GLN-LYS-OH, and H-TYR-ASN-ALA-GLN-LYS-OH were also disclosed to possess activity in the chicken assay of Examples XIV through XVI thereof at a concentration of 0.1 μg/ml (100 ng/ml).

Reference is made to the above-described patent and patent application for a discussion of other prior art and the biological processes involved in the present invention.

The present invention provides peptides which are at least as active as the prior art pentapeptides, while being significantly simpler in structure. These new peptides therefore have a significant advantage in ease and cost of manufacture. Some of these new peptides are surprisingly and significantly more active than the reference pentapeptides.

SUMMARY OF THE INVENTION

It is therefore one object of this invention to provide new peptides which have ubiquitin-like activity in that they induce differentiation of both T-precursor cells as well as B-precursor cells into T-cells and B-cells, respectively, and which are therefore highly useful in the immune system of humans and animals.

A further object is to provide peptides which are of simpler structure than other peptides having ubiquitin-like activity.

A still further object is to provide peptides having significantly greater potency than previously-known peptides having ubiquitin-like activity.

Other objects and advantages of the invention will become apparent as the description proceeds.

In satisfation of the foregoing objects and advantages there is provided by this invention the novel peptides of formula:

A-B wherein A is a member selected from the group consisting of deamino GLN, GLN, and $(SAR)_n$-GLN; n is an integer from 1 to 4; and B is a member selected from the group consisting of LYS-OH, LYS-NH$_2$, decarboxy LYS,

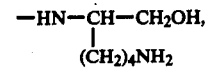

LYS-SAR-OH and LYS-SAR-NH$_2$. Also provided are therapeutic compositions containing these peptides and methods for administration of the peptides to humans or animals for effecting biological actions thereon.

The peptides wherein A is a member selected from the group consisting of deamino-GLN and GLN are of significantly simpler structure and ease of manufacture than the reference pentapeptides, since these materials are merely dipeptides or tripeptides. The peptides wherein A is a member selected from the group consisting of deamino-GLN and $(SAR)_n$-GLN, wherein n is 2, 3, or 4 and B is a member selected from the group consisting of LYS-OH and LYS-NH$_2$ are significantly more active than the reference pentapeptides, showing activity in the chicken induction assay set out below at concentrations of from about 10 femptograms (fg)/ml to about 100 ng/ml. Thus, these peptides are as much as 10 million times more potent than the reference pentapeptides. Since certain of these more potent peptides are also of very simple structure, they combine significantly increased potency with comparative ease and economy of manufacture.

DETAILED DESCRIPTION OF THE INVENTION

As indicated above, this invention is concerned with new peptides having therapeutic value in various areas, therapeutic compositions containing these peptides, and methods for use thereof.

In its broadest scope, the present invention provides peptides having the following formula:

A-B      I.

wherein A is a member selected from the group consisting of deamino GLN, GLN, and $(SAR)_n$-GLN; n is an integer from 1 to 4; and B is a member selected from the group consisting of LYS-OH, LYS-NH$_2$, decarboxy LYS,

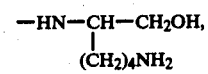

LYS-SAR-OH and LYS-SAR-NH$_2$. Also provided are therapeutic compositions and methods for use thereof.

Also included within the scope of the invention are the pharmaceutically acceptable salts of the peptides. As acids which are able to form salts with the peptides, there may be mentioned inorganic acids such as hydrochloric acid, hydrobromic acid, perchloric acid, nitric acid, thiocyanic acid, sulfuric acid, phosphoric acid, etc. and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalenesulfonic acid or sulfanilic acid, for instance.

In the above structures the amino acid components of the peptides are identified by abbreviations for convenience. These abbreviations are as follows:

| Amino Acid | Abbreviation |
|---|---|
| L-Glutamine | GLU |
| L-Alanine | ALA |
| L-Lysine | LYS |
| L-Tyrosine | TYR |
| L-Asparagine | ASN |
| L-Isoleucine | ILE |
| Sarcosine | SAR |

The terms "deamino-GLN" and "decarboxy-LYS" refer, respectively, to an L-glutamine residue in which the α-amino group has been replaced by hydrogen and an L-lysine residue in which the carboxyl group has been replaced by hydrogen. The formulas of these two moieties are, respectively, $H_2NOC-(CH_2)_3-CO-$ and $-HN-(CH_2)_5NH_2$.

The peptides of this invention contain the dipeptide moiety -GLN-LYS- either by itself or in combination with from one to five sarcosine radicals. These peptides have been found to exhibit characteristics similar to the 74 amino acid polypeptide ubiquitin disclosed in U.S. Pat. No. 4,002,602. The peptides of this invention are particularly characterized in their ability to induce the selective differentiation of T-precursor cells and B-precursor cells in as low as femptogram/ml concentrations. It is surprising that this dipeptide fragment, either alone or in combination with from one to five residues of the non-natural amino acid sarcosine, would possess any activity at all, let alone the surprisingly potent ubiquitin-like activity. The significance of this invention resides in the unique combination of extreme simplicity of the peptide and striking potency. That is, the least potent of the subject peptides (H-GLN-LYS-NH₂) has the same potency as the thymopoietin pentapeptide, while being only a dipeptide. The most potent of the subject peptides (H-SAR-SAR-SAR-GLN-LYS-NH₂) is approximately 10 million times more potent than the thymopoietin pentapeptide. Thus, the peptides of this invention, in concentrations as low as 10 femptograms per ml, have been found to induce the differentiation of both T-precursor cells as measured by the acquisition of the thymic differentiation antigens TL and THY-1 (θ), as well as B-precursor cells as measured by the acquisition of receptors for complement, a distinctive marker of B-cells.

To aid in the appreciation of the surprising potency of the subject peptides, the following table of measurements is provided.

| Measurement (Abbreviation) | Weight in grams |
|---|---|
| milligram (mg) | $10^{-3}$ |
| microgram (μg) | $10^{-6}$ |
| nanogram (ng) | $10^{-9}$ |
| picogram (pg) | $10^{-12}$ |
| femptogram (fg) | $10^{-15}$ |

A preferred embodiment of the subject peptides is that of formula (I) wherein A is a member selected from the group consisting of deamino GLN, and $H-(SAR)_n-GLN$; n is 2, 3, or 4; and B is a member selected from the group consisting of LYS-OH and LYS-NH₂. These preferred peptides exhibit activity at concentrations in the range from 10 fg/ml to about 100 ng/ml.

The peptide of sequence GLN-LYS-SAR-NH₂ may be represented chemically as:

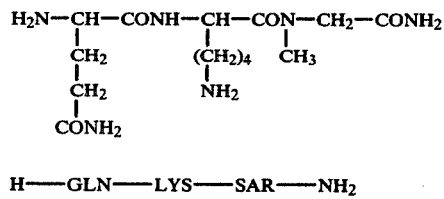

H——GLN——LYS——SAR——NH₂

A second preferred embodiment of the subject peptides is that of formula (deamino GLN)-LYS-C, where C is a member selected from the group consisting of OH and NH₂. These preferred peptides combine striking potency with extreme simplicity of structure and ease of preparation. These preferred dipeptides are of such simple structure that they can be crystallized, in contrast to larger peptides, which generally cannot. The ability to crystallize these dipeptides is an exceedingly significant factor in simplifying the purification thereof.

To provide an understanding of the importance of the differentiating biological characteristics of the peptides of this invention, it should be noted that the function of the thymus in relation to immunity may be broadly stated as the production of thymus-derived cells (lymphocytes), which are called T cells. T cells form a large proportion of the pool of recirculating small lymphocytes. T cells have immunological specificity and are directly involved in cell-mediated immune responses (such as homograft responses), as effector cells. T cells, however, do not secrete humoral antibodies. These antibodies are secreted by cells (termed B cells) derived directly from the bone marrow independently of the thymic influence. However, for many antigens, B cells require the presence of appropriately reactive T cells before they can produce antibodies. T cells are also involved in regulation of the immune system as helper cells, suppressor cells, etc. The mechanism of this process of cell cooperation is not yet completely understood.

From this explanation, it may be said that in operational terms, the thymus is necessary for the development of cellular immunity and many humoral antibody responses as well as for regulation of the immune system. These results are achieved, at least in part, by the induction, within the thymus, of the differentiation of haemopoietic stem cells to T cells. This inductive influence is mediated by secretions of the epithelial cells of the thymus, that is, by the thymic hormones.

Further, to understand the operation of the thymus and the cell system of lymphocytes, and the circulation of lymphocytes in the body, it should be pointed out that stem cells arise in the bone marrow and reach the thymus by the bloodstream. Within the thymus, stem cells become differentiated to immunologically competent T cells, which migrate to the bloodstream and together with B cells, circulate between the tissues, lymphatics, and the bloodstream.

The cells of the body which secrete antibody (the B cells) also develop from haemopoietic stem cells, but their differentiation is not determined by the thymus. In birds they are differentiated in an organ analogous to the thymus, which is called the Bursa of Fabricius. In mammals no equivalent organ has been discovered, and it is thought that B cells differentiate within the bone marrow. Hence, they are termed bone marrow derived cells or B cells. The physiological substances dictating this differentiation remain completely unknown.

As pointed out above, the peptides of this invention are therapeutically useful in the treatment of humans and animals. Since the new peptides have the capability of inducing the differentiation of lymphopoietic stem cells originating in the haemopoietic tissues to both thymus-derived lymphocytes (T cells) and immunocompetent B cells which are capable of involvement in the immune response of the body, the products of this invention are considered to have multiple therapeutic uses. Primarily, since the compounds have the capability of carrying out certain of the indicated functions of the thymus they have application in various thymic function and immunity areas. A primary field of application is in the treatment of DiGeorge Syndrome, a condition in which there is a congenital absence of thymus. Injection of the polypeptides will overcome this deficiency. Another application is in agammaglobulinemia, which is due to a defect of the putative B cell differentiative hormone of the body. Injection of the polypeptides will overcome this defect. Since the peptides are active at very low concentrations, they are useful in assisting the collective immunity of the body in that they increase or assist in therapeutic stimulation of cellular immunity and humoral immunity and thereby become useful in the treatment of diseases involving chronic infection in vivo, such as fungal or mycoplasma injections, tuberculosis, leprosy, acute and chronic viral infections and the like. Further, the peptides are considered to be useful in any area in which cellular or humoral immunity is an issue and particularly where there are deficiencies in immunity such as in the DiGeorge Syndrome mentioned above. Further, because of the characteristics of the peptides, they have in vitro usefulness in inducing the development of surface antigens of T cells, in inducing the development of the functional capacity to achieve responsiveness to mitogens and antigens and cell collaborativity in enhancing the ability of B cells to produce antibodies. They have in vitro usefulness in inducing the development of B cells as measured by the development of surface receptors for complement. The peptides are also useful in inhibiting the uncontrolled proliferation of lymphocytes which are responsive to ubiquitin (described in U.S. Pat. No. 4,002,602). An important characteristic of the peptides is their in vivo ability to restore cells with the characteristics of T cells and also their in vivo ability to restore cells with the characteristics of B cells. They are, therefore, useful in the treatment of relative or absolute B cell deficiencies as well as relative or absolute T cell deficiencies, whether or not these deficiencies are due to deficiencies in the tissue differentiating B cells or the thymus, respectively, or to some other cause.

A further important property of the peptides of this invention are that they are highly active in very low concentrations. Thus, it has been found that the peptides are generally active in concentrations of about 10 pg/ml–10 ng/ml, while the preferred peptides are active at concentrations ranging from about 10 fg/ml. The carrier may be any of the well-known carriers for this purpose including normal saline solutions, preferably with a protein diluent such as bovine serum albumin to prevent adsorptive losses to glassware at these low concentrations. The peptides of this invention are generally active at a range of above about 1 $\mu$g/kg of body weight, while the preferred peptides are active from about 10 pg/kg. For the treatment of DiGeorge Syndrome, the peptides may be administered at a rate of about 1 to about 100 $\mu$g/kg of body weight. Generally, the same range of dosage amounts may be used in treatment of the other conditions or diseases mentioned. While the above discussion has been given with respect to parenteral administration, it should be understood that oral administration is also possible at dosage ranges generally about 100 to 1000 times greater than those for injection. Other well-known routes of administration, e.g., —sublingual, rectal, nasal, etc., may also be employed.

To prepare the pharmaceutical compositions of the present invention, the peptide of formula (I) or an acid addition salt thereof is combined as the active ingredient in intimate admixture with a pharmaceutical carrier according to conventional pharmaceutical compounding techniques, which carrier may take a wide variety of forms depending on the form of preparation desired for administration, e.g., sublingual, rectal, nasal, oral, or parenteral. In preparing the compositions in oral dosage form, any of the usual pharmaceutical media may be employed, such as for example, water, glycols, oils, alcohols, flavoring agents, preservatives, coloring agents, and the like in the case of oral liquid preparations such as for example, suspensions, elixirs, and solutions; or carriers such as starches, sugars, diluents, granulating agents, lubricants, binders, disintegrating agents, and the like in a case of oral solid preparations, such as for example, powders, capsules, and tablets. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, although other ingredients, for example, to aid solubility or for preservative purposes, may be included. Injectable suspensions may also be prepared, in which case appropriate liquid carriers, suspending agents, and the like may be employed. The parenteral pharmaceutical compositions of the invention should be designed to administer the subject peptides at a rate of about 10 pg/kg to about 100 ng/kg of body weight. The oral compositions should administer about 100 to 1000 times the dose for parenteral administration—i.e., from about 1 ng/kg to about 100 $\mu$g/kg of body weight. Accordingly, the parenteral compositions should contain, per dosage unit, from about 500 pg to about 5 $\mu$g, whereas the oral compositions should contain, per dosage unit, from about 50 ng to about 5 mg of the subject peptide.

In view of the above it should be apparent that the present invention further comprises methods of treatment which comprise administartion of the subject peptides in therapeutically effective doses to patients in need of same.

Many of the peptides of this invention were prepared using concepts similar to those described by Merrifield as reported in *Journal of American Chemical Society*, 85, pp 2149–2154, 1963. The synthesis involved the stepwise addition of protected amino acids to a growing peptide chain which was bound by covalent bonds to a solid resin particle. By this procedure, reagents and by-products were removed by filtration and the purification of intermediates was eliminated. The general concept of this method depends on attachment of the C-terminal amino acid of the chain to a solid polymer by a covalent bond and the addition of the succeeding amino acids one at a time in a stepwise manner until the desired sequence is assembled. Finally the peptide is removed from the solid support and protective groups removed. This method provides a growing peptide chain attached to a completely insoluble solid particle so that it is in a convenient form to be filtered and washed free of reagents and by-products.

The amino acids may be attached to any suitable polymer which merely has to be readily separable from the unreacted reagents. The polymer may be insoluble in the solvents used or may be soluble in certain solvents and insoluble in others. The polymer should have a stable physical form permitting ready filtration. It must contain a functional group to which the first protected amino acid can be firmly linked by a covalent bond. Various insoluble polymers suitable for this purpose are those such as cellulose, polyvinyl alcohol, polymethacrylate and sulfonated polystyrene but in the synthesis of this invention, there was used a chloromethylated copolymer of styrene and divinylbenzene. Polymers which are soluble in organic solvents while being insoluble in aqueous solvents may also be used. One such polymer is a polyethylene/glycol having a molecular weight of about 20,000, which is soluble in methylene chloride but insoluble in water. The use of this polymer in peptide synthesis is described in F. Bayer and M. Mutter, *Nature*, 237, 512 (1972) and references contained therein.

The various functional groups on the amino acid which were active, but which were not to enter into the reactions, were protected by conventional protecting groups as used in the polypeptide art throughout the reaction. Thus, the functional group on lysine was protected by protecting groups which could be removed on completion of the sequence without adversely affecting the polypeptide final product. In the synthesis ninhydrin was used to determine if coupling was complete. If complete coupling was not indicated, the coupling was repeated with the same protected amino acid before deprotection.

The C-terminal amino acid may be attached to the polymer in a variety of well-known ways. Summaries of methods for attachment to halomethyl resins are given in Horiki, et al., *Chem. Letters*, pp 165–168 (1978) and Gisin, *Helv. Chim. Acta*, 56, 1476 (1973), and references given therein. If a C-terminal amide is to be prepared, one of two routes may be employed. Either the peptide resin prepared according to the Merrifield technique may be cleaved from the resin using anhydrous ammonia, or a benzhydrylamine resin may be employed. Cleavage from this latter resin with hydrogen fluoride affords the C-terminal amide peptide. The use of a benzhydrylamine resin is shown in, for example, J. Rivier, et al., *J. Med. Chem.*, 16, pp 545–549 (1973).

The general procedure for preparation of C-terminal carboxyl peptides involved intially esterifying L-lysine, protected on its amino groups, to the chloromethyl resin by the $CsHCO_3$ method referred to in the above Gisin article. The protecting group on the α-amino group of the lysine amino acid (e.g., t-BOC, i.e., t-butyloxycarbonyl), was then removed without affecting other protecting groups. The coupled amino acid resin was then filtered, washed, and neutralized. The resulting coupled amino acid resin, having the free amino group, was then reacted with a protected L-glutamine, preferably alpha-t-BOC-L-glutamine to couple the L-glutamine. The sequence of reactions was carried out as follows:

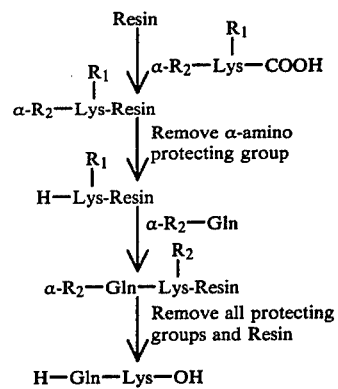

In the above sequence of reactions $R_1$ is a protecting group on the reactive side chain on the L-lysine which is not affected or removed when the protective group on the α-amino group is removed to permit further reaction and α-$R_2$ is a protecting group on the α-amino group. Preferably in the above intermediate pentapeptide resin, the term $R_1$ stands for a protective grouping such as 2-chlorobenzyloxycarbonyl and $R_2$ stands for t-butyloxycarbonyl. The resin is any of the resins mentioned above as being useful in the process.

After the final intermediate is prepared, the peptide-resin is cleaved to remove the $R_1$ and $R_2$ protecting groups thereon and the resin. The protecting groups are removed by conventional means, e.g., by treatment with anhydrous hydrogen fluoride, and the resulting free peptide was then recovered.

As pointed out above, in conducting the process it is necessary to protect or block the amino groups in order to control the reaction and obtain the products desired. Suitable amino-protecting groups which may be usefully employed include salt formation for protecting strongly-basic amino groups, or urethane protecting substitutes such as benzyloxycarbonyl and t-butyloxycarbonyl. It is preferred to utilize t-butyloxycarbonyl (t-BOC) or t-amyloxycarbonyl (AOC) for protecting the α-amino group in the amino acids undergoing reaction at the carboxyl end of the molecule, since the BOC and AOC (t-amyloxycarbonyl) protecting groups are readily removed following such reaction and prior to the subsequent step (wherein such α-amino group itself undergoes reaction) by relatively mild action of acids (e.g., trifluoroacetic acid), which treatment does not otherwise affect groups used to protect other reactive side chains. It will thus be understood that the α-amino groups may be protected by reaction with any material which will protect the amino groups for the subsequent reaction(s) but which may later be removed under conditions which will not otherwise affect the molecule. Illustrative of such materials are organic carboxylic or carbonic acid derivatives which will acylate the amino group.

In general, any of the amino groups can be protected by reaction with a compound containing a grouping of the formula:

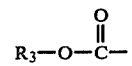

wherein R₃ is any grouping which will prevent the amino group from entering into subsequent coupling reactions and which can be removed without destruction of the molecule. Thus R₃ is a straight or branched chain alkyl which may be unsaturated, preferably of 1 to 10 carbon atoms and preferably halo- or cyano-substituted, aryl, preferably of 6 to 14 carbons, cycloalkyl, preferably of 5 to 8 carbon atoms; aralkyl, preferably of 7 to 18 carbon atoms, alkaryl, preferably of 7 to 18 carbon atoms, or heterocyclic e.g., isonicotinyl. The aryl, aralkyl and alkaryl moieties may also be further substituted as by one or more alkyl groups of 1 to about 4 carbon atoms. Preferred groupings for R₃ include t-butyl, t-amyl, phenyl, tolyl, xylyl and benzyl. Highly preferred specific amino-protecting groups include benzyloxycarbonyl; substituted benzyloxycarbonyl wherein the phenyl ring is substituted by one or more halogens, e.g., Cl or Br, nitro, loweralkoxy, e.g., methoxy, or loweralkyl; t-butyloxycarbonyl, t-amyloxycarbonyl; cyclohexyloxycarbonyl; vinyloxycarbonyl; adamantyloxycarbonyl; bisphenylisopropoxycarbonyl; and the like. Other protecting groups which can be used include isonicotinyloxycarbonyl, phthaloyl, p-tolylsulfonyl, formyl and the like.

In conducting the general process of the invention, the peptide is built by reaction of the free α-amino group with a compound possessing protected amino groups. For reaction or coupling, the compound being attached is activated at its carboxyl group so that the carboxyl group can then react with the free α-amino group on the attached peptide chain. To achieve activation the carboxyl group can be converted to any reactive group such as an ester, anhydride, azide, acid chloride, or the like. Alternately, a suitable coupling reagent may be added during the reaction. Suitable coupling reagents are disclosed, e.g., in Bodanszky, et al.—*Peptide Synthesis*, Interscience, second edition, 1976, chapter five, including carbodiimides (e.g., dicyclohexylcarbodiimide), carbonyldiimidizole, and the like.

It should also be understood that during these reactions, the amino acid moieties contain both amino groups and carboxyl groups and usually one grouping enters into the reaction while the other is protected. Prior to the coupling step, the protecting group on the alpha or terminal amino group of the attached peptide is removed under conditions which will not substantially affect other protecting groups, e.g., the group on epsilonamino of the lysine molecule. The preferred procedure for effecting this step is mild acidolysis, as by reaction at room temperature with trifluoroacetic acid.

As may be appreciated, the above-described series of process steps results in the production of the specific peptide of the following formula:

H-GLN-LYS-OH    II.

Preparation of the corresponding sarcosine-containing peptides may be accomplished by the same sequence of reactions as above, in which protected sarcosine is added at the appropriate part(s) of the procedure. In this way peptides of the following formulas may be prepared: H-SAR-GLN-LYS-OH, H-SAR-SAR-GLN-LYS-OH, H-SAR-SAR-SAR-GLN-LYS-OH, H-SAR-SAR-SAR-SAR-GLN-LYS-OH, and H-GLN-LYS-SAR-OH. Peptides of formula (I) wherein A is deamino GLN may be prepared by substituting protected deamino GLN for GLN in the above-described procedures. Thus may be prepared deamino GLN-LYS-OH, and deamino GLN-LYS-SAR-OH.

Peptides of formula (I) in which B is LYS-NH₂ or LYS-SAR-NH₂ may be prepared by the above-described procedure, but substituting for the chloromethyl resin used therein a benzhydrylamine resin. In this way, C-terminal amide peptides corresponding to the above-described C-terminal carboxy peptides may be prepared. An alternate method of preparing these peptide amides is to cleave from the chloromethyl resin using anhydrous ammonia.

While the solid phase technique of Merrifield has been used to prepare the subject polypeptides, it is clearly contemplated that classical techniques described in, for example, the above-referenced Bodanszky, et al., text, may also be employed. As an example of this method, deamino-GLN-LYS-OH was prepared using solution techniques as shown in Example IX below. Those compounds of formula (I) wherein B is decarboxy-LYS or

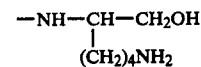

are not readily prepared using the solid phase techniques of Merrifield due to the lack of a carboxyl group to couple the GLN amino acid derivative to the resin. These compounds are conveniently prepared as follows. The compound of formula (I) wherein B is decarboxy-LYS may be prepared by reacting 1,5-diaminopentane with an active ester of the suitably protected A group (e.g., α-amino protected L-glutamine active ester), followed by removal of the protecting groups and purification. The preparation of active esters of amino acids is well-known in the peptide synthesis art.

The compound of formula (I) wherein B is

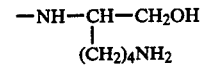

may be prepared by reacting suitably protected starting material of formula (III) with a suitably protected A group (e.g., α-amino protected L-glutamine active ester), followed by removal of protective groups and purification. This reaction is illustrated by the following:

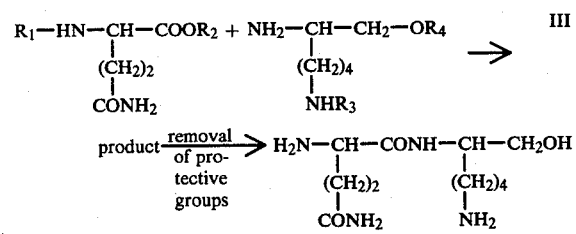

wherein R₁ and R₃ are (e.g.) benzyloxycarbonyl, R₄ is (e.g.) benzyl, and R₂ is an active ester group such as (e.g.) p-nitrophenyl or p-nitrothiophenyl.

The identity, purity, and sequence of the subject peptides were determined by the well-known techniques of thin-layer chromatography, electrophoresis, amino acid analysis, nuclear magnetic resonance spectroscopy, elemental analysis, infrared spectroscopy, and the like.

11

The following examples are presented to illustrate the invention, but it is not to be considered as limited thereto. In the examples, and throughout the specification, parts are by weight unless otherwise indicated.

EXAMPLE I

In preparation of one peptide of this invention the following materials were purchased commercially.
Alpha-BOC-L-Glutamine
Alpha-BOC-ε-benzyloxycarbonyl-L-lysine In these reagents, BOC is t-butyloxycarbonyl. "Sequenal" grade reagents for amino acid sequence determination, dicyclohexylcarbodiimide (DCC), ninhydrin, and the resin were purchased commercially. The resin used was a benzhydrylamine resin having a capacity of 0.5 meq/g of resin.

In preparation of the peptide, α-BOC-ε-benzyloxycarbonyl-L-lysine was coupled to the benzhydrylamine resin using DCC as the coupling reagent. The resulting protected amino acid resin contained 0.4–0.5 mmole of amino acid per gram of resin. Using a Schwarz/Mann Automatic Peptidee Synthesizer, the following program was used to couple each BOC-protected amino acid to the BOC-amino acid resin:

1. Prewashing with 40% trifluoroacetic acid (TFA) in $CH_2Cl_2$, once, 1.5 min.
2. Deprotection with 40% TFA in $CH_2Cl_2$, once, 20 min.
3. Washing with $CHCl_3$, once, 1.5 min.
4. Washing with EtOH, once, 1.5 min.
5. Washing with $CH_2Cl_2$, twice, 1.5 min.
6. Prewashing with 10% $Et_3N$ in $CH_2Cl_2$, once, 1.5 min.
7. Neutralization with 10% $Et_3N$ in $CH_2Cl_2$, once, 10 min.
8. Washing with $CH_2Cl_2$, three times, 1.5 min.
9. Addition of BOC-protected amino acid (5 molar excess) in dimethylformamide (DMF) and $CH_2Cl_2$ (1:9 vol./vol.).
10. Addition of DCC in $CH_2Cl_2$ (0.5 M 5 molar excess), the reaction time was up to 2 hours.
11. Washing with $CH_2Cl_2$, twice, 1.5 min.

Thereafter, the α-BOC amino acids were similarly coupled to the deprotected α-amino group of the peptide-resin in the correct sequence to result in a peptide of this invention using equivalent amounts of dicyclohexyl carbodiimide. After each coupling reaction, an aliquot of resin was tested with ninhydrin and if a positive result was found, coupling was taken to be incomplete and was repeated with the same protected amino acid. As the result of a single coupling reaction using α-BOC-L-glutamine, the following peptide-resin resulted:

where BOC is butyloxycarbonyl and CBZ is benzyloxycarbonyl.

This peptide-resin was cleaved and the protecting groups removed in a Kel-F cleavage apparatus (Peninsula Laboratories, Inc.) using 10 ml anhydrous hydrogen fluoride per gram of resin at 0° C. for 60 minutes with 5 ml anisole per gram peptide-resin as scavenger. After evaporation in vacuo to dryness, the residue was washed with anhydrous ether. The crude peptide was dissolved in 10% aqueous acetic acid and filtered. The resin was washed with 10% aqueous acetic acid and the combined filtrates were collected and lyophilized to give crude peptide. The crude peptide was purified by countercurrent distribution using n-butanol-acetic acid:water (4:1:5) as the partition phase to afford the pure peptide. The resulting peptide has the following sequence:

For identification, thin layer chromatography and electrophoresis were employed. The amino acid composition was determined using an amino acid analyzer.

Thin layer chromatography was performed on 20 μg samples on silica gel (Kieselgel, 5×20 cm) using 1:1:1:1 n-butanol:acetic acid:ethyl acetate:water as the solvent system ($R_f^1$) and on cellulose 6064 (Eastman 20×20 cm) using 15:10:3:12 n-butanol:pyridine:acetic acid:water as the solvent system ($R_f^2$). The $R_f^1$ values relative to H-ARG-LYS-ASP-VAL-TYR-OH were $R_f^1=1.16$ and $R_f^2=0.57$. Ninhydrin was used as a spray reagent.

Electrophoresis was performed on a 100 μg sample on Whitman No. 3 paper (5.7×55 cm) using a pH 5.6 pyridine-acetate buffer at a voltage of 1000 V for 1.0 hours. The pentapeptide had a mobility of 2.21 toward the cathode relative to H-ARG-LYS-ASP-VAL-TYR-OH. Ninhydrin and Pauly spray reagents were used.

EXAMPLE II

To determine the activity and characteristics of the peptide of Example I, determinations were carried out on healthy 5–6 week nu/nu mice of both sexes, the mice being bred on a BALB/c background (thymocytes expressing Thy-1.2 surface antigen) and maintained under conventional conditions. For the antisera, anti Thy-1.2 sera were prepared in Thy-1 congenic mice.

For the induction in vitro of Thy-1+ T cells or CR+ B cell differentiation, the induction of thymocyte differentiation from prothymocytes in vitro was performed as described by Komuro and Boyse, (*Lancet*, 1, 740, 1973), using the acquisition of Thy-1.2 as a marker of T cell differentiation. The induction of CR+ B cell differentiation from CR− B cell precursors in vitro was performed under similar conditions using as the assay criterion, the capacity of CR+ B cells to bind sheep erythrocytes coated with subagglutinating quantities of rabbit antibody and nonlytic complement. Spleen cell populations from healthy nu/nu mice fractionated on discontinuous bovine serum albumin gradients were used as the source of both precursor types (Thy-1− and CR−) because they have few or no Thy-1+ cells and low numbers of CR+ cells.

As a result of this determination it was found that the peptide displayed a selectivity of actions similar to that of ubiquitin in inducing the differentiation of Thy-1+ T-lymphocytes and of complement receptors (CR+) B-lymphocytes in concentrations ranging from 10 ng/ml to 10 μg/ml.

EXAMPLES III—VII

Following the procedure of Example I but employing protected sarcosine (e.g., α-BOC-sarcosine) at the appropriate steps, there are prepared the following:

| Example | Compound |
|---------|----------|
| III | H—GLN—LYS—SAR—NH₂ |
| IV | H—SAR—GLN—LYS—NH₂ |
| V | H—SAR—SAR—GLN—LYS—NH₂ |

-continued

| Example | Compound |
|---|---|
| VI | H—SAR—SAR—SAR—GLN—LYS—NH₂ |
| VII | H—SAR—SAR—SAR—SAR—GLN—LYS—NH₂ |

The sequence of these peptides was determined by an amino acid analyzer. Thin layer chromatography and electrophoresis under the same conditions as in Example I yielded the following information:

| Example | $R_f^1$ | $R_f^2$ | Mobility toward cathode |
|---|---|---|---|
| III | 0.73 | 0.52 | 1.52 (2 hrs) |
| IV | 1.16 | 0.57 | 2.04 |
| V | 0.83 | 0.61 | 1.88 |
| VI | 0.5 | 0.58 | 1.83 |
| VII | 0.32 | 0.54 | 1.98 (2 hrs) |

All $R_f$ and electrophoresis values are relative to the reference peptide H-ARG-LYS-ASP-VAL-TYR-OH.

EXAMPLE VIII

Following the procedure of Example II, the compounds of Examples III–VII were evaluated for their ability to induce the differentiation of Thy-1+ T-lymphocytes and CR+ B-lymphocytes. The activity ranges are given below:

| Compound Example No. | Active Concentration Range |
|---|---|
| III | 100 pg/ml–100 ng/ml |
| IV | 1–10 μg/ml |
| V | 100 pg/ml–10 ng/ml |
| VI | 10 fg/ml–100 pg/ml |
| VII | 1–100 pg/ml |

EXAMPLE IX

To a suspension of N^ε-benzyloxycarbonyl-L-lysine (20.0 g; 0.0713 M) in pyridine (400 ml) was added at 0° C. in an N₂ atmosphere, methyl 4-(chloroformyl)-butyrate (12.9 g; 0.0785 M) with vigorous stirring. The mixture was stirred for 1.5 hr at 0° C. and 0.5 hr at 23° C. The pyridine was removed at reduced pressure to give a crude yellow oil (38 g) which was chromatographed on SilicAR CC-7 (600 g). Elution with 1–3% MeOH/CHCl₃ gave a light yellow oil (30.6 g) which was rechromatographed on SilicAR CC-7 (900 g). Elution with 1–3% MeOH/CHCl₃ gave a clear colorless oil (24.3 g). This material was recrystallized twice from 2:1 EtOAc/hexane to give a white solid, m.p. 64°–66° C., which is deamino-GLU-OMe-N^ε-benzyloxycarbonyl-LYS.

To a solution of this white solid (5.0 g; 0.018 M) in MeOH (200 ml) was added Pd/C 10% (500 mg). The mixture was hydrogenated at 40 psi for 4 hrs, filtered and the solvent removed at reduced pressure to give a white solid (3.6 g) which was recrystallized from 10:1 MeOH:Et₂O to give a white solid, m.p. 203°–204° C., which is deamino-GLU-OMe-LYS.

This product (200 mg, 0.00073 M) was dissolved in conc. NH₄OH (58%, 10 ml) and the mixture stirred for 16 hrs at 23° C. The solvent was removed at reduced pressure to give a white solid (190 mg) which was recrystallized from 10:4:1 MeOH:Et₂O:H₂O to give deamino-GLN-LYS as a white solid (100 mg), m.p. 235 (dec.); nmr (D₂O) ε, 1.75 (m, 8H, methylene H),

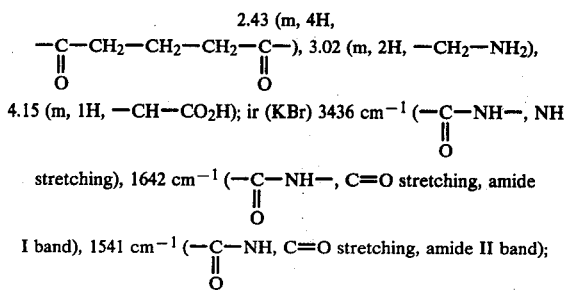

4.15 (m, 1H, —CH—CO₂H); ir (KBr) 3436 cm⁻¹ (—C(=O)—NH—, NH stretching), 1642 cm⁻¹ (—C(=O)—NH—, C=O stretching, amide I band), 1541 cm⁻¹ (—C(=O)—NH, C=O stretching, amide II band);

M.S. (probe): m/e 259 (parent peak).

Anal. Calcd for $C_{11}H_{21}N_3O_4$: C, 50.95; H, 8.16; N, 16.20. Found: C, 51.10; H, 8.28; N, 15.96.

EXAMPLES X–XI

Following the procedure of Examples I and III, but substituting for the protected L-glutamine used therein an equivalent amount of deamino-glutamine, there are prepared the following:

| Example | Formula |
|---|---|
| X | deamino-GLN—LYS—NH₂ |
| XI | deamino-GLN—LYS—SAR—NH₂ |

EXAMPLE XII

Following the procedure of Examples I, III–VII, and X–XI but substituting for the benzhydrylamine resin used therein a polystyrene divinylbenzene resin containing 1% divinylbenzene and 0.75 mM of chloride per gram of resin, there are prepared the C-terminal carboxyl peptides corresponding to the C-terminal amide peptides prepared in the reference example.

EXAMPLES XIII–XXII

Following the procedure of either Example XIII or XIV but substituting for the protected L-glutamine used therein an equivalent amount of one of the following (suitably protected): deamino-glutamine, Sar-GLN, SAR-SAR-GLN, SAR-SAR-SAR-GLN, and SAR-SAR-SAR-SAR-GLN, there are prepared the following:

| Example No. | Compound Formula |
|---|---|
| XIII | deamino-GLN-decarboxy-LYS |
| XIV | H—SAR—GLN-decarboxy-LYS |
| XV | H—SAR—SAR—GLN-decarboxy-LYS |
| XVI | H—SAR—SAR—SAR—GLN-decarboxy-LYS |
| XVII | H—SAR—SAR—SAR—SAR—GLN-decarboxy-LYS |
| XVIII | deamino-GLN—HN—CH—CH₂OH<br>                                \|<br>                          (CH₂)₄—NH₂ |

-continued

| Example No. | Compound Formula |
|---|---|
| XIX | H—SAR—GLN—HN—CH(—(CH$_2$)$_4$—NH$_2$)—CH$_2$OH |
| XX | H—SAR—SAR—GLN—NH—CH(—(CH$_2$)$_4$—NH$_2$)—CH$_2$OH |
| XXI | H—SAR—SAR—SAR—GLN—HN—CH(—(CH$_2$)$_4$—NH$_2$)—CH$_2$OH |
| XXII | H—SAR—SAR—SAR—SAR—GLN—HN—CH(—(CH$_2$)$_4$—NH$_2$)—CH$_2$OH |

The peptides prepared in Examples X–XXII have the biological activity as described in Example II.

The invention has been described herein with reference to certain preferred embodiments. However, as obvious variations will appear to those skilled in the art, the invention is not to be considered as limited thereto.

What is claimed is:

1. A peptide possessing ubiquitin-like activity having the formula:

A-B wherein A is a member selected from the group consisting of deamino GLN, GLN, and (SAR)$_n$-GLN; n is an integer from 1 to 4; and B is a member selected from the group consisting of LYS-OH, LYS-NH$_2$, decarboxy-LYS, $$-HN-CH(-(CH_2)_4NH_2)-CH_2OH,$$

LYS-SAR-OH and LYS-SAR-NH$_2$, provided that when A is GLN, B is other than LYS-OH, and the pharmaceutically-acceptable acid addition salts thereof.

2. The peptide of claim 1 wherein A is a member selected from the group consisting of deamino-GLN, and H-(SAR)$_n$-GLN; n is 2, 3, or 4; and B is a member selected from the group consisting of LYS-OH and LYS-NH$_2$.

3. The peptide of claim 1 of formula (deamino-GLN)-LYS-C, where C is a member selected from the group consisting of OH and NH$_2$.

4. A peptide of formula H-SAR-SAR-GLN-LYS-NH$_2$ and the pharmaceutically-acceptable salts thereof.

5. A peptide of formula H-SAR-SAR-SAR-GLN-LYS-NH$_2$ and the pharmaceutically-acceptable salts thereof.

6. A peptide of formula H-SAR-SAR-SAR-SAR-GLN-LYS-NH$_2$ and the pharmaceutically-acceptable salts thereof.

7. A peptide of formula H-SAR-GLN-LYS-NH$_2$ and the pharmaceutically-acceptable salts thereof.

8. A peptide of formula H-GLN-LYS-NH$_2$ and the pharmaceutically-acceptable salts thereof.

9. A peptide of formula deamino-GLN-LYS-OH and the pharmaceutically-acceptable salts thereof.

10. A therapeutic composition of matter comprising a therapeutically effective amount of the peptide of claim 1 in a pharmaceutically-acceptable carrier.

11. A therapeutic composition of matter for parenteral administration comprising in a pharmaceutically acceptable carrier from about 10 pg/kg to about 100 ng/kg body weight of a peptide having the formula A-B wherein A is a member selected from the group consisting of deamino GLN, GLY, and (SAR)$_n$-GLN; n is an integer from 1 to 4; and B is a member selected from the group consisting of LYS-OH, LYS-NH$_2$, decarboxy-LYS, $$-HN-CH(-(CH_2)_4NH_2)-CH_2OH,$$

LYS-SAR-OH and LYS-SAR-NH$_2$, or a pharmaceutically-acceptable acid addition salt thereof.

12. A therapeutic composition of matter for oral administration comprising in a pharmaceutically acceptable carrier from about 1 ng/kg to about 100 μg/kg body weight of a peptide having the formula A-B wherein A is a member selected from the group consisting of deamino GLN, GLY, and (SAR)$_n$-GLN; n is an integer from 1 to 4; and B is a member selected from the group consisting of LYS-OH, LYS-NH$_2$, decarboxy-LYS, $$-HN-CH(-(CH_2)_4NH_2)-CH_2OH,$$

LYS-SAR-OH and LYS-SAR-NH$_2$, or a pharmaceutically-acceptable acid addition salt thereof.

13. A method for the treatment of conditions resulting from relative or absolute T cell deficiencies which comprises administration of a therapeutically effective amount of a peptide having the formula A-B wherein A is a member selected from the group consisting of deamino GLN, GLY, and (SAR)$_n$-(GLN; n is an integer from 1 to 4; and B is a member selected from the group consisting of LYS-OH, LYS-NH$_2$, decarboxy-LYS, $$-HN-CH(-(CH_2)_4NH_2)-CH_2OH,$$

LYS-SAR-OH and LYS-SAR-NH$_2$, or a pharmaceutically-acceptable acid addition salt thereof.

14. A method for the treatment of conditions resulting from relative or absolute B cell deficiencies which comprises administration of a therapeutically effective amount of a peptide having the formula A-B wherein A is a member selected from the group consisting of deamino GLN, GLY, and (SAR)$_n$-GLN; n is an integer from 1 to 4; and B is a member selected from the group consisting of LYS-OH, LYS-NH$_2$, decarboxy-LYS,

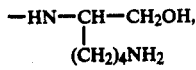

LYS-SAR-OH and LYS-SAR-NH$_2$, or a pharmaceutically-acceptable acid addition salt thereof.

15. A method for inducing bone marrow cells to develop the characteristics of thymus-derived lymphocytes which comprises administration of a therapeutically effective amount of a peptide having the formula A-B wherein A is a member selected from the group consisting of deamino GLN, GLY and (SAR)$_n$-GLN; n is an integer from 1 to 4; and B is a member selected from the group consisting of LYS-OH, LYS-NH$_2$, decarboxyl-LYS

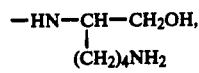

LYS-SAR-OH and LYS-SAR-NH$_2$, or a pharmaceutically-acceptble acid addition salt thereof.

16. A method for inducing bone marrow cells to develop the characteristics of immunocompetent B cells which comprises administration of a therapeutically effective amount of a peptide having the formula A-B wherein A is a member selected from the group consisting of deamino GLN, GLY, and (SAR)$_n$-GLN; n is an integer from 1 to 4; and B is a member selected from the group consisting of LYS-OH, LYS-NH$_2$, decarboxy-LYS,

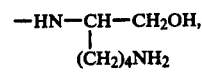

LYS-SAR-OH and LYS-SAR-NH$_2$, or a pharmaceutically-acceptable acid addition salt thereof.

17. A method for affecting the immune response in the body to assist in the correction of relative or absolute deficiencies of the thymus which comprises administration of a therapeutically effective amount of a peptide having the formula A-B wherein A is a member selected from the group consisting of deamino GLN, GLY, and (SAR)$_n$-GLN; n is an integer from 1 to 4; and B is a member selected from the group consisting of LYS-OH, LYS-NH$_2$, decarboxy-LYS,

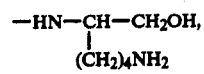

LYS-SAR-OH and LYS-SAR-NH$_2$, or a pharmaceutically-acceptable acid addition salt thereof.

18. A method for affecting the immune response in the body to assist in the correction of relative or absolute deficienices of the body tissues which differentiate B cells which comprises administration of a therapeutically effective amount of a peptide having the formula A-B wherein A is a member selected from the group consisting of deamino GLN, GLY, and (SAR)$_n$-GLN; n is an integer from 1 to 4; and B is a member selected from the group consisting of LYS-OH, LYS-NH$_2$, decarboxy-LYS,

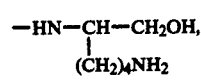

LYS-SAR-OH and LYS-SAR-NH$_2$, or a pharmaceutically-acceptable acid addition salt thereof.

19. A peptide of formula H-GLN-LYS-SAR-NH$_2$ and the pharmaceutically-acceptable salts thereof.

* * * * *

UNITED STATES PATENT AND TRADEMARK OFFICE
CERTIFICATE OF CORRECTION

PATENT NO. : 4,215,111
DATED : July 29, 1980
INVENTOR(S) : Gideon Goldstein and George Heavner It is certified that error appears in the above-identified patent and that said Letters Patent are hereby corrected as shown below:

In claims 11-18 please delete "GLY" and insert therefor --GLN--.

Signed and Sealed this

Twelfth Day of March 1985

[SEAL]

Attest:

DONALD J. QUIGG

Attesting Officer        Acting Commissioner of Patents and Trademarks